United States Patent [19]
Travers et al.

[11] 4,456,775
[45] Jun. 26, 1984

[54] CATALYTIC PROCESS FOR MANUFACTURING ALCOHOLS BY HYDROGENOLYSIS OF CARBOXYLIC ACID ESTERS

[75] Inventors: Christine Travers, Rueil-Malmaison; Chan Trinh Dinh, Le Vesinet; Roger Snappe, Sevres; Jean-Paul Bournonville, Chatou, all of France

[73] Assignee: Institut Francais du Petrole, Rueil-Malmaison, France

[21] Appl. No.: 497,631

[22] Filed: May 24, 1983

[30] Foreign Application Priority Data

May 24, 1982 [FR] France ................................ 82 09099

[51] Int. Cl.$^3$ ........................................... C07C 29/136
[52] U.S. Cl. .................................... 568/885; 502/242; 502/261; 502/332
[58] Field of Search ......................................... 568/885

[56] References Cited

U.S. PATENT DOCUMENTS

| 2,322,095 | 6/1943 | Schmidt | 568/885 |
|---|---|---|---|
| 3,769,331 | 10/1973 | Kuckertz et al. | 568/885 |
| 3,829,448 | 8/1974 | Kanetaka et al. | 568/885 |
| 4,104,478 | 8/1978 | Triredi | 568/885 |
| 4,273,947 | 6/1981 | Novotny | 568/885 |
| 4,338,221 | 7/1982 | Qualeatti | 568/885 |

FOREIGN PATENT DOCUMENTS

| 712197 | 6/1965 | Canada | 568/885 |
|---|---|---|---|
| 1518181 | 2/1968 | France | 568/885 |

OTHER PUBLICATIONS

Grimm et al., "J. Am. Oil Chemists Soc.", vol. 46, No. 2, p. 118, (1968).

Primary Examiner—J. E. Evans
Attorney, Agent, or Firm—Millen & White

[57] ABSTRACT

Alcohols and particularly fatty alcohols are manufactured by hydrogenolysis of carboxylic esters in the presence of a catalyst comprising a carrier, rhodium and at least one second element selected from the group consisting of tin, germanium and lead. The rhodium content is from 0.1 to 5% b.w. and the content of the second element is from 0.1 to 10% b.w.

16 Claims, No Drawings

CATALYTIC PROCESS FOR MANUFACTURING ALCOHOLS BY HYDROGENOLYSIS OF CARBOXYLIC ACID ESTERS

This invention relates to a catalytic process for manufacturing alcohols by hydrogenolysis of carboxylic esters.

The manufacture of alcohols, particularly of fatty alcohols, is of great industrial significance.

The catalytic hydrogenolysis of carboxylic esters is an attractive manner of manufacturing these alcohols; however it has been limited up to now by the poor performances of the known catalysts:

the catalysts comprising mixed copper and chromium oxides, with or without additives, require working under high pressure, in nearly all cases above 200 atmospheres, and at a temperature of 250° to 350° C., the catalysts comprising supported transition metals oblige to operate at a temperature lower than 250° C. and preferably lower than 200° C., to limit the degradation of the resultant alcohol to hydrocarbons, which requires operating pressures above 100 bars to obtain good selectivities at an acceptable conversion level.

It has surprisingly been discovered that the hydrogenation of an ester to an alcohol can be performed without structural modification of the hydrocarbon chain, according to the following scheme:

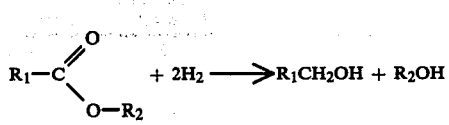

where $R_1$=saturated or unsaturated hydrocarbyl radical of 1–20 carbon atoms and $R_2$=alkyl of 1–10 carbon atoms, preferably methyl or ethyl. The operation is preferably performed in a continuous or a batch reactor under a total pressure of 10 to 100 bars, preferably 30 to 80 bars, although the pressure can be as high as 300 bars, without disadvantage, at a temperaure of 180° to 330° C. and preferably 200° to 280° C. and with a hydrogen to ester molar ratio of 2 to 10, more advantageously 2 to 5, in the presence of a supported metal catalyst comprising the following elements: rhodium, in a proportion b.w. from 0.1 to 5% and preferably from 0.5 to 2%, and at least one element selected from the group consisting of germanium, tin and lead in a proportion from 0.1 to 10% and more particularly from 2 to 5%.

Two of the above metals or even these three metals can advantageously be used together; the carrier can be selected from the group consisting of silica, different types of alumina, silica-aluminas, coal, and preferably from the group of the different aluminas. The use of an alumina carrier containing 1–5% of alkali metal (Na, K) or alkaline-earth metal (Mg, Ca, Ba) is also contemplated.

The catalyst can be prepared by different techniques of carrier impregnation and the invention is not limited to a particular technique. The impregnation operation consists, for example, of contacting the preformed carrier with an aqueous or organic solution of the one or more selected metal compounds, the volume of solution being in excess to the absorption volume of the carrier or equal to this volume. Rhodium and the additional metal can be introduced simultaneously or successively. After having contacted the carrier with the solution for several hours, the impregnated carrier is filtered, washed with distilled water, dried and calcined in the air at 110° to 600° C. and preferably 110° to 500° C. Before use, the catalyst is reduced under hydrogen at 200°–600° C. and preferably 300°–500° C., this reduction being effected immediately after the calcination or later, by the user.

The element selected from the group consisting of tin, germanium and lead may be introduced in aqueous solution or in hydrocabon solution, depending on the nature of the precursor. It is preferred to introduce rhodium first and to calcine or calcine and reduce, in the conditions described above, and to thereafter introduce tin, germanium and/or lead.

Another method consists of malaxing the wet carrier powder with the catalyst precursors and to shape and dry thereafter.

Examples of metal precursors for use in the manufacture of the catalyst are the following:

Rhodium can be used as compounds, such as chlorides, nitrates or salts of organic acids soluble in the impregnation solvent, for example rhodium chloride, rhodium nitrate, soluble salts of organic acids such as rhodium acetate, or alternatively hexammine rhodium chloride or nitrate. Organometal compounds of rhodium can also be used as a solution in a hydrocarbon, for example in a saturated paraffinic hydrocarbon whose hydrocarbon chain comprises 6 to 12 carbon atoms, in a naphthenic hydrocarbon comprising 6 to 12 carbon atoms or in an aromatic hydrocarbon comprising 6 to 11 carbon atoms; preference will be given to rhodium acetylacetonate.

The element selected from the group consisting of tin, germanium and lead may be introduced in the form of such compounds as tin chlorides, bromides and nitrate, lead halides, nitrate, acetate and carbonate, germanium chloride and oxalate, in aqueous solution, or preferably in the form of tin, germanium and lead alkyl-, cycloalkyl or aryl-metals, such as, for example: tetrabutyl tin, tetramethyl tin, tetrapropyl germanium, tetraethyl lead, diphenyl tin, diphenyl germanium or tetraphenyl lead, in hydrocarbon solution.

The carrier may be of various nature, as hereinbefore mentioned. A particularly well adapted carrier has the following specific characteristics: a specific surface, determined by the B.E.T. method, between 10 and 500 sq. m. per gram and preferably between 50 and 500 sq. m. per gram and a total pore volume between 20 and 130 cm³ per 100 g of carrier and preferably between 50 and 110 cm³ per 100 g of carrier.

Once the two metals have been attached to the carrier, the catalyst is usefully subjected to an activation treatment under hydrogen at a high temperature, for example 300°–500° C., in order to obtain an active metal phase. This treatment under hydrogen can be conducted, for example, by slowly increasing the temperature, under hydrogen stream, up to the maximum reduction temperature, comprised for example between 300° and 500° C. and preferably between 350° and 450° C., and thereafter maintaining this temperature for 1 to 6 hours.

The following non-limitative examples illustrate the invention.

EXAMPLE 1

The catalyst is manufactured in two steps:

adding rhodium by impregnating alumina with an aqueous solution of rhodium trichloride, this alumina having a specific surface of 200 m² per gram and a total pore volume of 60 cm³ per 100 grams, followed with filtration, drying at 110° C., calcining at 450° C. in the air and reducing with hydrogen at 450° C., fixing tin onto the carrier preimpregnated with rhodium, calcined and reduced, as tetraethyl tin dissolved in n-heptane. After having contacted the catalyst with the tetraethyl tin solution at the heptane reflux for 4 hours, the catalyst is washed with heptane and dried.

The catalyst is then introduced into a tubular reactor and reduced for 4 hours at 300° C. in a hydrogen stream.

The operating conditions of the ethyl acetate hydrolysis are the following:
pressure: 50 bars
VVH: 4 l/l of catalyst/hour
$H_2$/ester molar ratio: 5

In this first test series, the tin content of the catalysts has been varied from a basic catalyst containing 1% b.w. of rhodium. The working temperature was 250° C. The results are given in Table 1.

TABLE 1

| Rh (% b.w.) | Sn (% b.w.) | TOTAL CONVERSION (% b.w.) | YIELD (ETHANOL) (% b.w.) |
|---|---|---|---|
| 1 | 0 | 92 | 2.0 |
| 1 | 0.5 | 3 | 2.2 |
| 1 | 0.8 | 6 | 5.5 |
| 1 | 1.5 | 13.6 | 12.8 |
| 1 | 2.3 | 25.6 | 22.1 |
| 1 | 3.2 | 31.6 | 30.7 |

EXAMPLE 2

The catalytic properties of two catalysts have been compared at different temperatures with respect to the hydrogenolysis of ethyl acetate: one of them comprised 1% of rhodium on alumina, according to example 1, the other one comprised 1% of rhodium and 3.2% of tin on the same alumina carrier. The other conditions were those of example 1.

The results are given in Table 2.

TABLE 2

| | CATALYST | | | |
|---|---|---|---|---|
| | 1% Rh/Al$_2$O$_3$ | | 1% Rh + 3.2% Sn Al$_2$O$_3$ | |
| TEMPERATURE °C. | CONVERSION % b.w. | YIELD (ETHANOL) % b.w. | CONVERSION % b.w. | YIELD (ETHANOL) % b.w. |
| 200 | 2.6 | 1.7 | 6.6 | 6.5 |
| 220 | 19.4 | 6.0 | 16.0 | 15.8 |
| 250 | 92 | 2.0 | 31.6 | 30.7 |
| 280 | 100 | 0 | 70.7 | 66.3 |

In the whole temperature range, it is found that the bimetallic rhodium-tin on alumina catalyst is far more selective for the alcohol production.

EXAMPLE 3

The object is to manufacture ethanol from ethyl acetate in the same conditions as in example 1. The catalyst comprises 1% rhodium on the alumina of example 1 and a second element of the group: tin, germanium and lead.

Germanium and lead are introduced by impregnation from respectively tetraethyl germanium and tetraethyl lead as a solution in a hydrocarbon (n-heptane).

The resultant catalysts are used in the same manner as in example 1 (T=250° C., P=50 bars, VVH=4, $H_2$/ester molar ratio=5).

The results are given in Table 3.

TABLE 3

| Rh (% b.w.) | SECOND METAL (% b.w.) | CONVERSION (% b.w.) | YIELD (ETHANOL) (% b.w.) |
|---|---|---|---|
| 1 | 0 | 92 | 2.0 |
| 1 | Sn = 3.2 | 31.6 | 30.7 |
| 1 | Ge = 3.1 | 30.9 | 30.5 |
| 1 | Pb = 3.4 | 31.9 | 30.6 |

Tin can thus be replaced with germanium and lead without significant alteration of the catalytic properties of the active mass.

EXAMPLE 4

There are prepared, according to the method of example 1, catalysts comprising rhodium and tin on silica having a specific surface of 450 m²/g and a total pore volume of 80 cc per 100 grams. The hydrogenolysis of ethyl acetate has been effected under conditions identical to those of example 1.

The results are given in Table 4.

TABLE 4

| RHODIUM (% b.w.) | TIN (% b.w.) | CONVERSION (% b.w.) | YIELD (ETHANOL) (% b.w.) | SELECTIVITY (ETHANOL) (% b.w.) |
|---|---|---|---|---|
| 1 | 0 | 7 | 2.2 | 31.5 |
| 1 | 0.8 | 8.6 | 8.4 | 97.7 |
| 1 | 1.5 | 17.4 | 17.0 | 97.7 |
| 1 | 3.0 | 11.1 | 10.7 | 96.3 |

The selectivities of the conversion to alcohol are very high, in all cases higher than 95%.

EXAMPLE 5

A number of alcohols are manufactured from various esters in the presence of a catalyst (1% Rh+3.2% Sn+1.5% K on alumina) and under operating conditions identical to those of example 1.

The esters are the following:
sec. butyl acetate
amyl acetate
hexyl acetate
ethyl caproate
methyl palmitate
methyl oleate.

The results are summarized in Table 5.

TABLE 5

| SUBSTRATE | RESULTANT ALCOHOLS | CONVERSION (% b.w.) | ALCOHOLS YIELD (% b.w.) |
|---|---|---|---|
| Sec. butyl acetate | Ethanol and 2-butanol | 30.5 | 29.0 |
| Isoamyl acetate | Ethanol and isoamyl alcohol | 33.0 | 31.5 |
| Hexyl acetate | Ethanol and 1-hexanol | 32.0 | 30.0 |
| Ethyl caproate | 1-decanol and ethanol | 35.0 | 33.1 |
| Methyl palmitate | 1-hexadecanol and methanol | 32 | 30.5 |
| Methyl oleate | 1-octadecanol and methanol | 34 | 32.8 |

What is claimed is:

1. In a process for manufacturing alcohols, wherein an ester of a carboxylic acid is treated with hydrogen in the presence of a catalyst, the improvement wherein the catalyst comprises a carrier, rhodium, and at least one second element, being tin, germanium, lead or a mixture thereof.

2. A process according to claim 1, wherein the rhodium content of the catalyst is from 0.1 to 5% b.w. and the content of the second element is from 0.1 to 10% b.w.

3. A process according to claim 1, wherein the rhodium content of the catalyst is from 0.5 to 2% b.w. and the content of the second element is from 2 to 5% b.w.

4. A process according to claim 1 wherein the carrier has a surface of 10 to 500 m²/g and a pore volume of 0.2 to 1.3 cc/g.

5. A process according to claim 1, wherein the carrier has a surface of 50 to 500 m²/g and a pore volume of 0.5 to 1.1 cc/g.

6. A process according to claim 1, wherein the carrier is alumina.

7. A process according to claim 1, wherein the carrier is silica.

8. A process according to claim 1, wherein the pressure is from 10 to 100 bars and the temperature from 180° to 330° C.

9. A process according to claim 1, wherein the pressure is from 30 to 80 bars and the temperature from 200° to 280° C.

10. A process according to claim 1, wherein the molar ratio hydrogen/ester is from 2:1 to 10:1.

11. A process according to claim 10, wherein said molar ratio is from 2:1 to 5:1.

12. A process according to claim 1, wherein the carrier has a specific surface of 10–500 m²/g.

13. A process according to claim 12, wherein said specific surface is 50–500 m²/g.

14. A process according to claim 1, wherein the carrier has a total pore volume of 20–130 cm³ per 100 g of carrier.

15. A process according to claim 14, wherein said pore volume is 50–110 cm³ per 100 g of carrier.

16. A process according to claim 1, wherein said ester has the formula $R_1$—$COOR_2$, wherein $R_1$ is a saturated or unsaturated $C_{1-20}$ hydrocarbyl group, and $R_2$ is $C_{1-10}$ alkyl.

* * * * *